(12) United States Patent
Jeng et al.

(10) Patent No.: US 11,976,018 B2
(45) Date of Patent: May 7, 2024

(54) DIAMINE COMPOUND, METHOD FOR MANUFACTURING THE SAME, AND APPLICATIONS THEREOF

(71) Applicant: DAXIN MATERIALS CORP., Taichung (TW)

(72) Inventors: Kai-Sheng Jeng, Taichung (TW); Yuan-Li Liao, Taichung (TW); You-Ming Chen, Taichung (TW); Yu-Ying Kuo, Taichung (TW); Shao-Chi Cheng, Taichung (TW)

(73) Assignee: DAXIN MATERIALS CORP., Taichung (TW)

( * ) Notice: Subject to any disclaimer, the term of this patent is extended or adjusted under 35 U.S.C. 154(b) by 469 days.

(21) Appl. No.: 17/195,961

(22) Filed: Mar. 9, 2021

(65) Prior Publication Data

US 2021/0284596 A1      Sep. 16, 2021

(30) Foreign Application Priority Data

Mar. 10, 2020    (TW) ................................ 109107887

(51) Int. Cl.
*C07C 217/90*    (2006.01)
*C07C 213/02*    (2006.01)
*C08G 73/10*     (2006.01)

(52) U.S. Cl.
CPC .......... *C07C 217/90* (2013.01); *C07C 213/02* (2013.01); *C08G 73/1071* (2013.01)

(58) Field of Classification Search
CPC . C07C 217/90; C07C 213/02; C08G 73/1071; C08J 2379/08
See application file for complete search history.

(56) References Cited

U.S. PATENT DOCUMENTS

| 4,829,058 A | 5/1989 | Seydel et al. |
| 5,084,449 A | 1/1992 | Seydel et al. |

FOREIGN PATENT DOCUMENTS

| CN | 103172531 A | 6/2013 |
| CN | 103571500 A | 2/2014 |

(Continued)

OTHER PUBLICATIONS

Fujieda et al., Liquid crystal alignment agent, liquid crystal alignment film, and liquid crystal display element, TW201947029, provided by applicant on IDS, Translated copy of equivalent JP2019189416A1 utilized for the OA is attached for reference as NPL. (Year: 2019).*

(Continued)

*Primary Examiner* — Heidi R Kelley
*Assistant Examiner* — Surbhi M Du
(74) *Attorney, Agent, or Firm* — Nixon & Vanderhye PC (57) ABSTRACT

Disclosed is a diamine compound represented by Formula (1),

Formula (1)

$$H_2N-R^1\left[\underset{(X^1)_a}{\underset{|}{\bigcirc}}-R^4-\underset{(X^3)_c}{\underset{|}{\bigcirc}}\right]_m\left[R^3-\underset{(X^4)_d}{\underset{|}{\bigcirc}}-R^5\right]_n\underset{(X^2)_b}{\underset{|}{\bigcirc}}-R^2-NH_2$$

in which R1, R2, R3, R4, R5, X1, X2, X3, X4, m, n, a, b, c, and d are as defined herein. Also disclosed are a method for manufacturing the diamine compound, a composition including the diamine compound having a (chain alkoxy-methylene) phenyl group or a (hydroxyl-methylene) phenyl group, and a polymer including the (Continued)

(chain alkoxy-methylene) phenyl group or the (hydroxyl-methylene) phenyl group.

17 Claims, 3 Drawing Sheets

(56) References Cited

FOREIGN PATENT DOCUMENTS

| CN | 105969404 A | 9/2016 |
|---|---|---|
| JP | S60-255760 | 12/1985 |
| TW | 200914491 | 4/2009 |
| TW | 201947029 | 12/2019 |
| TW | 202104559 | 2/2021 |

OTHER PUBLICATIONS

Berger et al. Synthesis of Nitrogen-Doped ZigZag-Edge Peripheries: Dibenzo-9aazaphenalene as Repeating Unit, Angew. Chem. Int. Ed. 2014, 53, 10520-10524 (Year: 2014).*

Search Report for TW 109107887 dated Feb. 1, 2021, 3 pages, with an English translation.

Matthew C. Davis, "Convenient Preparation of Hydroxymethyl-Substituted Diaminodiphenyloxybenzenes," Synthetic Communications, 39, pp. 654-663, Jan. 2009.

Jin Chul Jung and Sang-Bong Park, "Synthesis, characterization and properties of polyimides from 3,3', 4,4'-benzophenonetetracarboxylic dianhydride and imidazoleblocked 2,5-bis[(n-alkyloxy)methyl]-1,4-benzenediisocyanates," Polymer Bulletin, 35, pp. 423-430, May 1995.

Search Report appended to an Office Action, which was issued to Taiwanese counterpart application No. 109107887 by the TIPO dated Sep. 14, 2021, with an English translation thereof, 4 pages.

M. E. Wright et al., "Synthesis of Hydroxymethyl-Functionalized Polyimides and the Facile Attachment of an Organic Dye Utilizing Bis(isocyanates) and Bis(acid chloride) Linkers," Macromolecules, 38(24), pp. 10014-10021, 2005.

Office Action issued to Korean counterpart application No. 10-2021-0029904 by the KIPO dated May 10, 2023, with an English translation thereof.

* cited by examiner

DIAMINE COMPOUND, METHOD FOR MANUFACTURING THE SAME, AND APPLICATIONS THEREOF

CROSS-REFERENCE TO RELATED APPLICATION

This application claims priority of Taiwanese Invention Patent Application No. 109107887, filed on Mar. 10, 2020.

FIELD

This disclosure relates to a diamine compound, and more particularly to a diamine compound including a (chain alkoxy-methylene) phenyl group or a (hydroxyl-methylene) phenyl group. This disclosure also relates to a method for manufacturing the diamine compound, and applications of the diamine compound.

BACKGROUND

Diamine compounds are commonly used as raw materials for producing functional polymeric materials, such as polyimide or polybenzimidazole. These functional polymeric materials are widely applied in various fields as, for example, an alignment film for a liquid crystal display device, a carrier film or a flexible substrate for a copper foil substrate in a printed circuit board, or an insulation film or a wiring film for a semiconductor package, etc. With increasing demand in these fields, the mechanical strengths of the functional polymeric materials have been improved, however, elongation rates of the functional polymeric materials remains unsatisfactory, resulting in poor stretchability thereof, thereby failing to meet industrial needs. Therefore, it still remains a goal to find a balance between the mechanical strengths and the elongation rates of the functional polymeric materials.

SUMMARY

Therefore, an object of the disclosure is to provide a diamine compound, a method for manufacturing the same, and applications thereof, so as to alleviate or eliminate at least one of the drawbacks of the prior art.

According to a first aspect of the disclosure, a diamine compound is represented by Formula (1),

Formula (1)

wherein each of $R^1$ and $R^2$ represents independently a single bond or a divalent aliphatic group which is uninterrupted or interrupted by a $T^1$ group representing a —O— group, a group, a group, or a group;

each of $R^3$, $R^4$, and $R^5$ represents independently a single bond, a hydrocarbylene group, an alkylene ether group, a —S— group, a —O— group, a group, a group, a group, a —C(CF$_3$)$_2$— group, or a —SO$_2$— group;

each of $X^1$, $X^2$, $X^3$, and $X^4$ represents independently hydrogen, a —CH$_2$—O-T$^2$ group, a —OH group, a —COOH group, an alkyl group, a halo group, a haloalkyl group, or an aryl group, wherein $T^2$ in the —CH$_2$—O-T$^2$ group represents hydrogen or a chain alkyl group;

each of m and n is independently an integer of from 0 to 6; and each of a, b, c, and d is independently an integer of from 0 to 4, with the proviso that when m>1, $R^4$s are the same or different, when n>1, $R^5$s are the same or different, when the number of $T^1$ is plural, $T^1$s are the same or different and at least two of $T^1$s are not bonded to each other, when the number of $T^2$ is plural, $T^2$s are the same or different, when a>1, $X^1$s are the same or different, when b>1, $X^2$s are the same or different, when c>1, $X^3$s are the same or different, when d>1, $X^4$s are the same or different,
at least one of a, b, c, and d is not 0,
at least one of $X^1$, $X^2$, $X^3$, and $X^4$ is the —$CH_2$—O-$T^2$ group, and
the diamine compound does not include a compound represented by a structural formula of

According to a second aspect of the disclosure, a method for manufacturing a diamine compound includes the steps of:

a) subjecting a compound represented by Formula (a) and a compound represented by Formula (b) to a reaction so as to obtain a compound represented by Formula (2); and
b) subjecting the compound represented by Formula (2) to a reduction reaction so as to obtain a compound presented by Formula (I), Formula (a)

Formula (b)

wherein
R represents $R^1$ or $R^2$, and each of $R^1$ and $R^2$ represents independently a single bond or a divalent aliphatic group which is uninterrupted or interrupted by a $T^1$ group representing a —O— group, a group, a group, or a group;
each of Y, $Y^1$, and $Y^2$ represents a leaving group;
X represents $(X^1)_a$ or $(X^1)_b$;
each of $X^1$, $X^2$, $X^3$, and $X^4$ represents independently hydrogen, a —$CH_2$—O-$T^2$ group, a —OH group, a —COOH group, an alkyl group, a halo group, a haloalkyl group, or an aryl group, wherein $T^2$ in the —$CH_2$—O-$T^2$ group represents hydrogen or a chain alkyl group;
each of $R^3$, $R^4$, and $R^5$ represents independently a single bond, a hydrocarbylene group, an alkylene ether group, a —S— group, a —O— group, a Formula (2)

Formula (1)

group, a group, a group, a —C(CF$_3$)$_2$— group, or a —SO$_2$— group;

each of m and n is independently an integer of from 0 to 6; and each of a, b, c, and d is independently an integer of from 0 to 4, with the proviso that when m>1, R$^4$s are the same or different, when n>1, R$^5$s are the same or different, when the number of T$^1$ is plural, T$^1$s are the same or different and at least two of T$^1$s are not bonded to each other, when the number of T$^2$ is plural, T$^2$s are the same or different, when a>1, X$^1$s are the same or different, when b>1, X$^2$s are the same or different, when c>1, X$^3$s are the same or different, when d>1, X$^4$s are the same or different, at least one of a, b, c, and d is not 0, and at least one of X$^1$, X$^2$, X$^3$, and X$^4$ is the —CH$_2$—O-T$^2$ group.

According to a third aspect of the disclosure, a composition for forming a polymer includes a diamine component which includes the diamine compound. The diamine compound has a functional group selected from the group consisting of a (chain alkoxy-methylene) phenyl group and a (hydroxyl-methylene) phenyl group.

According to a fourth aspect of the disclosure, a polymer includes a diamine structural unit which includes a functional group selected from the group consisting of a (chain alkoxy-methylene) phenyl group and a (hydroxyl-methylene) phenyl group.

According to a fifth aspect of the disclosure, a resin composition includes the polymer.

According to a sixth aspect of the disclosure, a product is made from the resin composition.

According to a seventh aspect of the disclosure, an electronic device includes the product.

Since the diamine compound of this disclosure includes a (chain alkoxy-methylene) phenyl group or a (hydroxyl-methylene) phenyl group, a polymer made from a diamine component including the diamine compound may have a satisfactory elongation at break and mechanical strength.

BRIEF DESCRIPTION OF THE DRAWINGS

Other features and advantages of the disclosure will become apparent in the following detailed description of the embodiment(s) with reference to the accompanying drawings, in which.

DETAILED DESCRIPTION

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described. For clarity, the following definitions are used herein.

According to the disclosure, a diamine compound is represented by Formula (1),

Formula (1)

wherein each of R$^1$ and R$^2$ represents independently a single bond or a divalent aliphatic group which is uninterrupted or interrupted by a T$^1$ group representing a —O— group, a group, a group, or a group;

each of $R^3$, $R^4$, and $R^5$ represents independently a single bond, a hydrocarbylene group, an alkylene ether group, a —S— group, a —O— group, a group, a group, a group, a —C(CF$_3$)$_2$— group, or a —SO$_2$— group;

each of $X^1$, $X^2$, $X^3$, and $X^4$ represents independently hydrogen, a —CH$_2$—O-T$^2$ group, a —OH group, a —COOH group, an alkyl group, a halo group, a haloalkyl group, or an aryl group, wherein T$^2$ in the —CH$_2$—O-T$^2$ group represents hydrogen or a chain alkyl group;

each of m and n is independently an integer of from 0 to 6; and each of a, b, c, and d is independently an integer of from 0 to 4, with the proviso that when m>1, $R^4$s are the same or different, when n>1, $R^5$s are the same or different, when the number of $T^1$ is plural, $T^1$s are the same or different and at least two of $T^1$s are not bonded to each other, when the number of $T^2$ is plural, $T^2$s are the same or different, when a>1, $X^1$s are the same or different, when b>1, $X^2$s are the same or different, when c>1, $X^3$s are the same or different, when d>1, $X^4$s are the same or different, at least one of a, b, c, and d is not 0, at least one of $X^1$, $X^2$, $X^3$, and $X^4$ is the —CH$_2$—O-T$^2$ group, and the diamine compound does not include a compound represented by a structural formula of

Examples of the hydrocarbylene group may include, but are not limited to, a divalent aliphatic group and an arylene group. Examples of the divalent aliphatic group may include, but are not limited to, an alkylene group, an alkenylene group, and an alkynylene group. Examples of the alkylene group may include, but are not limited to, a chain alkylene group and a cycloalkylene group. Examples of the chain alkylene group may include, but are not limited to, a straight chain alkylene group and a branched chain alkylene group. Examples of the straight chain alkylene group may include, but are not limited to, a methylene group, an ethylene group, a propylene group, a butylene group, a pentylene group, and a hexylene group. Examples of the branched chain alkylene group may include, but are not limited to, an isopropylene group, a 1-ethyl-propylene group, a 1,1-dimethyl-propylene group, a 1,2-dimethyl-propylene group, a 2,2-dimethyl-propylene group, a 1-ethyl-1-methyl-propylene group, a 1-ethyl-2-methyl-propylene group, a 1,1,2-trimethyl-propylene group, a 1,2,2-trimethyl-propylene group, a sec-butylene group, an isobutylene group, an isopentylene group, a 1-methyl-pentylene group, a 2-methyl-pentylene group, a 3-methyl-pentylene group, a 4-methyl-pentylene group, a 1-ethyl-butylene group, a 2-ethyl-butylene group, a 1,1-dimethyl-butylene group, a 1,2-dimethyl-butylene group, a 1,3-dimethyl-butylene group, a 2,2-dimethyl-butylene group, a 2,3-dimethyl-butylene group, a 3,3-dimethyl-butylene group, and an isohexylene group. Examples of the cycloalkylene group may include, but are not limited to, a cyclopropylene group, a 1-ethyl-cyclopropylene group, a 2-ethyl-cyclopropylene group, a 1-propyl-cyclopropylene group, a 2-propyl-cyclopropylene group, a 1-isopropyl-cyclopropylene group, a 1-isopropyl-cyclopropylene group, a 1,2-dimethyl-cyclopropylene group, a 2,3-dimethyl-cyclopropylene group, a 1-ethyl-2-methyl-cyclopropylene group, a 2-ethyl-1-methyl-cyclopropylene group, a 2-ethyl-2-methyl-cyclopropylene group, a 2-ethyl-3-methyl-cyclopropylene group, a 1,2,2-trimethyl-cyclopropylene group, a 1,2,3-trimethyl-cyclopropylene group, a 2,2,3-trimethyl-cyclopropylene group, a cyclobutylene group, a 1-methyl-cyclobutylene group, a 2-methyl-cyclobutylene group, a 3-methyl-cyclobutylene group, a 1-ethyl-cyclobutylene group, a 2-ethyl-cyclobutylene group, a 3-ethyl-cyclobutylene group, a 1,2-dimethyl-cyclobutylene group, a 1,3-dimethyl-cyclobutylene group, a 2,2-dimethyl-cyclobutylene group, a 2,3-dimethyl-cyclobutylene group, a 2,4-dimethyl-cyclobutylene group, a 3,3-dimethyl-cyclobutylene group, a cyclopentylene group, a 1-methyl-cyclopentylene group, a 2-methyl-cyclopentylene group, a 3-methyl-cyclopentylene group, a cyclohexylene group, and a methyl-cyclohexylene group. Examples of the alkenylene group may include, but are not limited to, a 1,1-vinylene group a 1,2-vinylene group (—CH═CH—), a propene-1,3-diyl group (—CH═CH—CH$_2$—), a 1-methyl-1,2-vinylene group, a 1,2-vinylene-1,1-ethylene group a 1,2-vinylene-1,2-ethylene group (—CH═CH—CH$_2$—CH$_2$—), a 1,2-vinylene-1,2-propylene group, a 1,2-vinylene-1,3-propylene group, a 1,2-vinylene-1,4-butylene group, a 1,2-vinylene-1,2-butylene group, a 1,2-vinylene-1,2-heptenylene group and a 1,2-vinylene-1,2-decenylene group. Examples of the alkynylene group may include, but are not limited to, an ethynylene group, an ethynylene-methylene group an ethynylene-1,1-ethylene group an ethynylene-1,2-ethylene group an ethynylene-1,2-propylene group, an ethynylene-1,3-propylene group, an ethynylene-1,4-butylene group, an ethynylene-1,2-butylene group, an ethynylene-1,2-heptenylene group and an ethynylene-1,2-decenylene group. A non-limiting example of the alkylene ether group may be a -$(T^4)_t$-O— group, in which t is not less than 1, and $T^4$ represents an alkylene group. Examples of the alkylene group are as mentioned above and are thus not described in detail again for the sake of brevity. Examples of the alkyl group may include, but are not limited to, a chain alkyl group and a cycloalkyl group. Examples of the chain alkyl group may include, but are not limited to, a straight chain alkyl group and a branched chain alkyl group. Examples of the straight chain alkyl group may include, but are not limited to, a methyl group, an ethyl group, a propyl group, a butyl group, a pentyl group, and a hexyl group. Examples of the branched chain alkyl group may include, but are not limited to, an isopropyl group, a 1-ethyl-propyl group, a 1-ethyl-1-methyl-n-propyl group, a 1-ethyl-2-methyl-n-propyl group, a 1,1-dimethyl-propyl group, a 1,2-dimethyl-propyl group, a 2,2-dimethyl-propyl group, a 1,1,2-trimethyl-n-propyl group, a 1,2,2-trimethyl-n-propyl group, an isobutyl group, a sec-butyl group, a 1-ethyl-n-butyl group, a 2-ethyl-n-butyl group, a 1-methyl-butyl group, a 2-methyl-butyl group, a 3-methyl-butyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, an isopentyl group, a 1-methyl-pentyl group, a 2-methyl-pentyl group, a 3-methyl-pentyl group, and a 4-methyl-pentyl group. Examples of the cycloalkyl group may include, but are not limited to, a cyclopropyl group, a 1-methyl-cyclopropyl group, a 2-methyl-cyclopropyl group, a 1,2-dimethyl-cyclopropyl group, a 2,3-dimethyl-cyclopropyl group, a 1-ethyl-cyclopropyl group, a 2-ethyl-cyclopropyl group, a 1-propyl-cyclopropyl group, a 2-propyl-cyclopropyl group, a 1-isopropyl-cyclopropyl group, a 2-isopropyl-cyclopropyl group, a 1-ethyl-2-methyl-cyclopropyl group, a 2-ethyl-1-methyl-cyclopropyl group, a 2-ethyl-2-methyl-cyclopropyl group, a 2-ethyl-3-methyl-cyclopropyl group, a 1,2,2-trimethyl-cyclopropyl group, a 1,2,3-trimethyl-cyclopropyl group, a 2,2,3-trimethyl cyclopropyl group, a cyclobutyl group, a 1-methyl-cyclobutyl group, a 2-methyl-cyclobutyl group, a 3-methyl-cyclobutyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a cyclopentyl group, a 1-methyl-cyclopentyl group, a 2-methyl-cyclopentyl group, a 3-methyl-cyclopentyl group, and a cyclohexyl group. Examples of the halo group may include, but are not limited to, a fluoro group and a chloro group. Examples of the haloalkyl group may include, but are not limited to, a —$CF_3$ group, a —$CH_2F$ group, a —$CF_2H$ group, and a —$CCl_3$ group. Examples of the aryl group may include, but are not limited to, a phenyl group, a halo-substituted phenyl group, and a haloalkyl-substituted phenyl group, in which examples of the halo group and the haloalkyl group are as mentioned above and are thus not described in detail again for the sake of brevity. Examples of the divalent aliphatic group may include, but are not limited to, an alkylene group, an alkenylene group, a substituted alkenylene group, an alkynylene group, and a substituted alkynylene group, in which a non-limiting example of the substituent may be an alkyl group. Examples of the alkyl group and the alkylene group are as mentioned above and are thus not described in detail again for the sake of brevity.

In certain embodiments, the diamine compound includes a plurality of the —$CH_2$—O-$T^2$ groups so as to provide a better elongation rate for a polymer made of the diamine compound. When the diamine compound includes a plurality of the —CH—O-$T^2$ groups, in certain embodiments, $T^2$ may be a chain alkyl group (e.g., a —$CH_3$ group). In certain embodiments, a sum of m and n is at least 1 (i.e., m+n≥1). In certain embodiments, the sum of m and n ranges from 1 to 8 (i.e., 1≤m+n≤8). In certain embodiments, each of $R^4$ and $R^5$ is the —O— group. In certain embodiments, each of $X^1$ and $X^2$ is not the —$CH_2$—O-$T^2$ group. In certain embodiments, at least one of $X^1$, $X^2$, $X^3$, and $X^4$ is alkyl group, the halo group, or the haloalkyl group. That is, when a total number of $X^1$, $X^2$, $X^3$, and $X^4$ is plural, at least one of $X^1$, $X^2$, $X^3$, and $X^4$ is the —$CH_2$—O-$T^2$ group, and the remaining ones of $X^1$, $X^2$, $X^3$, and $X^4$ are independently selected from the group consisting of the alkyl group, the halo group, and the haloalkyl group.

In certain embodiments, examples of the diamine compound represented by Formula (I) include, but are not limited to, diamine compounds represented by the following structural formulae:

Formula (1-1)

Formula (1-2)

Formula (1-3)

Formula (1-4)

Formula (1-5)

Formula (1-6)

Formula (1-7)

Formula (1-8)

and

Formula (1-9)

According to the disclosure, a method for manufacturing a diamine compound includes the steps of:

a) subjecting a compound represented by Formula (a) and a compound represented by Formula (b) to a reaction so as to obtain a compound represented by Formula (2); and b) subjecting the compound represented by Formula (2) to a reduction reaction so as to obtain a compound presented by Formula (1), Formula (a)

Formula (b)

Formula (2)

Formula (1)

wherein

R represents $R^1$ or $R^2$, and each of $R^1$ and $R^2$ represents independently a single bond or a divalent aliphatic group which is uninterrupted or interrupted by a $T^1$ group representing a —O— group, a group, a group, or a group;

each of Y, $Y^1$, and $Y^2$ represents a leaving group;

X represents $(X^1)_a$ or $(X^1)_b$;

each of $X^1$, $X^2$, $X^3$, and $X^4$ represents independently hydrogen, a —$CH_2$—O-$T^2$ group, a —OH group, a —COOH group, an alkyl group, a halo group, a haloalkyl group, or an aryl group, wherein $T^2$ in the —$CH_2$—O-$T^2$ group represents hydrogen or a chain alkyl group;

each of $R^3$, $R^4$, and $R^5$ represents independently a single bond, a hydrocarbylene group, an alkylene ether group, a —S— group, a —O— group, a group, a group, a group, a —C(CF$_3$)$_2$— group, or a —SO$_2$— group;

each of m and n is independently an integer of from 0 to 6; and each of a, b, c, and d is independently an integer of from 0 to 4, with the proviso that when m>1, $R^4$s are the same or different, when n>1, $R^5$s are the same or different, when the number of $T^1$ is plural, $T^1$s are the same or different and at least two of $T^1$s are not bonded to each other, when the number of $T^2$ is plural, $T^2$s are the same or different, when a>1, $X^1$s are the same or different, when b>1, $X^2$s are the same or different, when c>1, $X^3$s are the same or different, when d>1, $X^4$s are the same or different, at least one of a, b, c, and d is not 0, and at least one of $X^1$, $X^2$, and $X^4$ is the —$CH_2$—O-$T^2$ group.

A non-limiting example of the leaving group may be a halo group. In certain embodiments, step a) is performed in the presence of a basic catalyst. Examples of the basic catalyst may include, but are not limited to, potassium carbonate, sodium hydroxide, and sodium bicarbonate. In certain embodiments, step a) is performed in the presence of a solvent. A non-limiting example of the solvent may be a polar solvent. Examples of the polar solvent may include, but are not limited to, N,N-dimethylacetamide, N-methyl-2-pyrrolidone (hereinafter abbreviated as NMP), γ-butyrolacetone (hereinafter abbreviated as GBL), N,N-diethylformamide, dimethyl sulfoxide, tetrahydrofuran, and ethyl acetate. In certain embodiments, step a) is performed at a temperature ranging from 70° C. to 140° C. In certain embodiments, the reduction reaction in step b) is performed in presence of a catalyst and a reducing agent to convert a nitro group into an amino group. Examples of the catalyst may include, but are not limited to, a palladium/carbon catalyst and a platinum catalyst. Examples of the reducing agent may include, but are not limited to, hydrazine and ammonium formate. In certain embodiments, step b) is performed in the presence of a solvent. A non-limiting example of the solvent may be a polar solvent. Examples of the polar solvent may include, but are not limited to, water, methanol, ethanol, propanol, isopropanol, tetrahydrofuran, ethyl acetate, NMP, GBL, N,N-diethylformamide, and dimethyl sulfoxide. In certain embodiments, step b) is performed at a temperature ranging from 50° C. to 80° C.

<Polymer>

According to the disclosure, a polymer includes a diamine structural unit which includes a functional group selected from the group consisting of a (chain alkoxy-methylene) phenyl group and a (hydroxyl-methylene) phenyl group. In an embodiment, the polymer is derived from the diamine compound of the disclosure, and has the (chain alkoxy-methylene) phenyl group or the (hydroxyl-methylene) phenyl group. The chain alkoxy-methylene group or the (hydroxyl-methylene) phenyl group is a side chain of the polymer so that the methylene group can serve as a cross-linking group between the polymer molecules. To be specific, for example, when the polymer molecule is exposed to an acidic or heating environment, a phenyl group on a polymer molecule will attack the methylene group of another polymer molecule, causing the chain alkoxy group or the hydroxyl group connected to the methylene group to leave, which allows the methylene group to bond with the phenyl group on the other polymer molecule, thereby improving an elongation rate of the polymer.

Examples of the polymer may include, but is not limited to, polyamide, polyamic acid, polyimide, polyamic ester, polyamide-imide, polybenzoxazole, a polybenzoxazole precursor, polybenzimidazole, and copolymers thereof.

A non-limiting example of the polyamic acid may be a polymer having a repeating unit represented by Formula (i), Formula (i)

in which $T^3$ is a tetravalent hydrocarbyl group, and $R^1$, $R^2$, $R^3$, $R^4$, $R^5$, $X^1$, $X^2$, $X^3$, $X^4$, m, n, a, b, c, and d are as defined above. Examples of the tetravalent hydrocarbyl group may include, but are not limited to, a tetravalent aryl group and a tetravalent aliphatic group. Examples of the tetravalent aryl group may include, but are not limited to, and

A non-limiting example of the polyimide may be a polymer having a repeating unit represented by Formula (ii), Formula (ii)

in which $T^4$ is a tetravalent hydrocarbyl group, and $R^1$, $R^2$, $R^3$, $R^4$, $R^5$, $X^1$, $X^2$, $X^3$, $X^4$, m, n, a, b, c, and d are as defined above. Examples of the tetravalent hydrocarbyl group may include, but are not limited to, a tetravalent aryl group and a tetravalent aliphatic group. Examples of the tetravalent aryl group may be those as described above.

Examples of the polybenzoxazole precursor may include, but are not limited to, a polymer having a repeating unit represented by Formula (iii), Formula (iii)

In Formula $T^5$ is a divalent hydrocarbyl group, each of a and b is independently an integer of from 0 to 3, each of $R^1$ and $R^2$ is a single bond, and $R^3$, $R^4$, $R^5$, $X^1$, $X^2$, $X^3$, $X^4$, m, n, c, and d are as defined above. Examples of the divalent hydrocarbyl group may include, but are not limited to, a divalent aryl group and a divalent aliphatic group. In certain embodiments, the divalent hydrocarbyl group is the divalent aryl group.

<Composition for Forming a Polymer>

According to the disclosure, a composition for forming a polymer includes a diamine component, which includes a diamine compound having a functional group selected from the group consisting of a (chain alkoxy-methylene) phenyl group and a (hydroxyl-methylene) phenyl group. In an embodiment, the diamine compound has the (chain alkoxy-methylene) phenyl group. The diamine compound having the (chain alkoxy-methylene) phenyl group may be, but is not limited to, the diamine compound of the disclosure which is represented by Formula (1).

The diamine component further includes other diamine compound. Examples of the other diamine compound may include, but are not limited to, 4,4'-bis(4-aminophenoxy) biphenyl (hereinafter abbreviated as APBP), 4-[4-[4-[4-amino-2-(trifluoromethyl)phenoxy]phenyl]phenoxy]-3-(trifluoromethyl)aniline (hereinafter abbreviated as DABP), 2,2-bis[4-(4-aminophenoxy)phenyl]propane (hereinafter abbreviated as BAPP), 4,4'-diaminodiphenyl ether (hereinafter abbreviated as ODA), 2,2-bis(3-amino-4-hydroxyphenyl)hexafluoropropane (hereinafter abbreviated as BisAPAF), 2,2-bis[4-(4-aminophenoxy)phenyl]hexafluoropropane (hereinafter abbreviated as 6FBAPP), 2,2'-dimethyl-(1,1'-biphenyl)-4,4'-diamine, 2,2'-bis(trifluoromethyl)-(1,1'-biphenyl)-4,4'-diamine, 9,9'-bis(3-fluoro-4-aminophenyl)fluorene, 1,3-bis(4-aminophenoxy)benzene, 1,4-bis(4-aminophenoxy)benzene, 1,3-bis(3-aminophenoxy)benzene, bis(2-trifluoromethyl-4-aminophenoxy)benzene, and 3,3'-dihydroxybenzidine.

In certain embodiments, the diamine compound having the (chain alkoxy-methylene) phenyl group is present in an amount of not greater than 0.1 mol based on 1 mol of the diamine component, so as to further improve the elongation rate of the polymer made from the composition. In certain embodiments, the diamine compound having the (chain alkoxy-methylene) phenyl group is present in an amount of not greater than 0.05 mol based on 1 mol of the diamine component.

The composition for forming the polymer further includes a reactive monomer which is reactive with amino groups. Examples of the reactive monomer may include, but is not limited to, a dianhydride compound, a carboxylic acid compound, a carboxylate compound, an aldehyde compound, an acyl chloride compound, an isocyanate compound, and combinations thereof. The dianhydride compound may be one that is used for manufacturing polyimide. Examples of the dianhydride compound may include, but are not limited to, 4,4'-(4,4'-isopropylidenediphenoxy)bis-(phthalic anhydride) (hereinafter abbreviated as BPADA) and 4,4'-oxydiphthalic anhydride (hereinafter abbreviated as ODPA). The carboxylic acid compound may be one that is used for manufacturing polybenzimidazole or polyamic ester. Examples of the carboxylic acid compound may include, but are not limited to, formic acid and an acid represented by a structural formula of

The aldehyde compound may be one that is used for manufacturing polybenzimidazole. A non-limiting example of the aldehyde compound may be benzaldehyde. The acyl chloride compound may be one that is used for manufacturing polybenzoxazole. Examples of the acyl chloride compound may include, but are not limited to terephthaloyl chloride, isophthaloyl chloride, phthaloyl chloride, and combinations thereof.

<Resin Composition>

According to the disclosure, a resin composition includes the abovementioned polymer. In certain embodiments, according to industrial requirements, the resin composition may further include a solvent. Examples of the solvent may include, but are not limited to, GEL, NMP, and the combination thereof. In certain embodiments, according to industrial requirements, the resin composition may further include an initiator. Examples of the initiator may include, but are not limited to, a photoinitiator and a thermal initiator. Examples of the photoinitiator may include, but are not limited to, commercially available products manufactured by BASF Corporation, such as Irgacure® OXE-01 {i.e., 1-[4-(phenylthio)phenyl]-1,2-octanedione 2-(O-benzoyloxime)}, Irgacure® OXE-02, Irgacure® TPO-L, and Irgacure® 819. In certain embodiments, according to industrial requirements, the resin composition may further include a reactive monomer. A non-limiting example of the reactive monomer may be an ethylenic monomer. Examples of the ethylenic monomer may include, but are not limited to, tri(ethylene glycol) diacrylate, tri(propylene glycol) dimethacrylate, tri(propylene glycol) diacrylate, 1,6-hexanediol dimethacrylate, 1,6-hexanediol diacrylate, ethoxylated bisphenol A dimethacrylate, ethoxylated bisphenol A diacrylate, and combinations thereof. In certain embodiments, according to industrial needs, for example, for improving a coatability of the resin composition, the resin composition may further include a surfactant. A non-limiting example of the surfactant may be a leveling agent. Examples of the leveling agent may include, but are not limited to, a silicon-containing material having an epoxide group, a silicon-containing material having an amino group, a fluoride material, and combinations thereof. By modifying the components of the resin composition, the resin composition may be used as a film-forming composition, a negative photoresist composition, a positive photoresist composition, or a photosensitive composition in a process for packaging a semiconductor device, a process for manufacturing a displayer, or a process for manufacturing a printed circuit board.

<Product>

According to the disclosure, a product is made from the abovementioned resin composition. Examples of the product may include, but are not limited to, a separation film, a cover film, a protective film, a carrier film, and an insulation film and a wiring film for a semiconductor packaging process. A method for forming the product is not limited specifically, and may be any well-known in the art, such as a coating method. Examples of the coating method may include, but are not limited to, spin coating, bar coating, roller coating, and die coating. In certain embodiments, when the product is required to be patterned, the method may further include a lithography process, which is not limited specifically, and may be any conventional lithography process.

<Electronic Device>

According to the disclosure, an electronic device includes the abovementioned product. Examples of the electronic device may include, but are not limited to, a semiconductor device and a display device.

The embodiments of the disclosure will now be explained in more detail hereinbelow by way of the following examples and comparative examples. Those examples are intended for purposes of illustration only and are not intended to limit the scope of the present disclosure.

<Example 1>

10.9 g of 3,3',5,5'-tetrakis(methoxymethyl)-(1,1'-biphenyl)-4,4'-diol, 9.12 g of potassium carbonate, and 165 mL of N,N-dimethylacetamide were added into a three-necked bottle having a stirrer. Then, the three-necked bottle was filled with nitrogen gas and sealed. Next, the content of the three-necked bottle was stirred well, followed by gradually adding 14.9 g of 2-chloro-5-nitrobenzotrifluoride into the three-necked bottle. Subsequently, the three-necked bottle was heated to a temperature of 140° C. to permit reaction for 3 hours, during which the reaction status was determined using thin-layer chromatography (hereinafter abbreviated as TLC). After the reaction was completed, potassium carbonate was removed by a suction filtration process to obtain a filtrate. Thereafter, the filtrate was gradually added into water to obtain an aqueous solution including precipitates, followed by subjecting the aqueous solution to another suction filtration process so as to obtain a light-pink solid precipitate. The light-pink solid precipitate was analyzed to be a dinitro compound represented by Formula (2-1).

Formula (2-1)

The dinitro compound represented by Formula (2-1) has a yield of 96% and a purity of 96%.

20.0 g of the dinitro compound represented by Formula (2-1), 0.43 g of a palladium/carbon catalyst, and 250 mL of ethanol were added into a three-necked bottle having a stirrer. Then, the content of the three-necked bottle was stirred under heating to a temperature of 60° C. Next, 17.3 g of hydrazine was gradually added into the three-necked bottle using a dropper, followed by heating to a temperature of 75° C. to permit hydrogenation reaction for 4 hours. Subsequently, the status of the reaction was determined using TLC, and after the reaction was completed, the palladium/carbon catalyst was removed by a suction filtration process to obtain a filtrate. Thereafter, the filtrate was gradually added into water to obtain an aqueous solution including precipitates, followed by subjecting the aqueous solution to another suction filtration process so as to obtain a white solid precipitate. The white solid precipitate includes the diamine compound represented by Formula (1-1).

Formula (1-1)

Finally, the white solid precipitate was subjected to a purification treatment using dichloromethane so as to obtain the diamine compound represented by Formula (1-1). The diamine compound represented by Formula (1-1) has a yield of 85% and a purity of 96%.

<Example 2>

10.9 g of 3,3',5,5'-tetrakis(methoxymethyl)-(1,1'-biphenyl)-4,4'-diol, 4.34 g of sodium hydroxide, and 165 mL of N,N-dimethylacetamide were added into a three-necked bottle having a stirrer. Then, the three-necked bottle was filled with nitrogen gas and sealed. Next, the content of the three-necked bottle was stirred well, followed by gradually adding 9.31 g of 4-fluoronitrobenzene into the three-necked bottle. Subsequently, the three-necked bottle was heated to a temperature of 140° C. to permit reaction for 3 hours, during which the reaction status was determined using TLC. After the reaction was completed, sodium hydroxide was removed by a suction filtration process to obtain a filtrate. Thereafter, the filtrate was gradually added into water to obtain an aqueous solution including precipitates, followed by subjecting the aqueous solution to another suction filtration process so as to obtain a solid precipitate. The solid precipitate was analyzed to be a dinitro compound represented by Formula (2-2).

Formula (2-2)

The dinitro compound represented by Formula (2-2) has a yield of 92% and a purity of 96%.

15.66 g of the dinitro compound represented by Formula (2-2), 0.43 g of a palladium/carbon catalyst, and 150 mL of ethanol were added into a three-necked bottle having a stirrer. Then, the content of the three-necked bottle was stirred under heating to a temperature of 60° C. Next, 17.3 g of hydrazine was gradually added into the three-necked bottle using a dropper, followed by heating to a temperature of 75° C. to permit hydrogenation reaction for 4 hours. Subsequently, the status of the reaction was determined using TLC, and after the reaction was completed, the palladium/carbon catalyst was removed by a suction filtration process to obtain a filtrate. Thereafter, the filtrate was gradually added into water to obtain an aqueous solution including precipitates, followed by subjecting the aqueous solution to another suction filtration process so as to obtain a white solid precipitate. The white solid precipitate was analyzed to be the diamine compound represented by Formula (1-2).

Formula (1-2)

The diamine compound represented by Formula (1-2) has a yield of 93% and a purity of 96%.

<Example 3>

9.48 g of 4,4'-methylenebis[6-methyl-2-(methoxymethylene)phenol, 6.3 g of sodium bicarbonate, and 60 mL of N,N-dimethylacetamide were added into a three-necked bottle having a stirrer. Then, the three-necked bottle was filled with nitrogen gas and sealed. Next, the content of the three-necked bottle was stirred well, followed by adding 13.53 g of 2-chloro-5-nitrobenzotrifluoride into the three-necked bottle. Subsequently, the three-necked bottle was heated to a temperature of 140° C. to permit reaction for 3 hours, during which the reaction status was determined using TLC. After the reaction was completed, sodium bicarbonate was removed by a suction filtration process to obtain a filtrate. Thereafter, the filtrate was gradually added into water to obtain an aqueous solution including precipitates, followed by subjecting the aqueous solution to another suction filtration process so as to obtain a brown solid precipitate. The brown solid precipitate was analyzed to be a dinitro compound represented by Formula (2-3).

Formula (2-3)

The dinitro compound represented by Formula (2-3) has a yield of 72% and a purity of 96%.

15.0 g of the dinitro compound represented by Formula (2-3), 0.21 g of a palladium/carbon catalyst, and 135 mL of ethanol were added into a three-necked bottle having a stirrer. Then, the content of the three-necked bottle was stirred under heating to a temperature of 50° C. Next, 10.89 g of ammonium formate was gradually added into the three-necked bottle using a dropper, followed by heating to a temperature of 60° C. to permit hydrogenation reaction for 4 hours. Subsequently, the status of the reaction was determined using TLC, and after the reaction was completed, the palladium/carbon catalyst was removed by a suction filtration process to obtain a filtrate. Thereafter, the filtrate was gradually added into water to obtain an aqueous solution including precipitates, followed by subjecting the aqueous solution to another suction filtration process so as to obtain a white solid precipitate. The white solid precipitate was analyzed to be the diamine compound represented by Formula (1-3).

Formula (1-3)

The diamine compound represented by Formula (1-3) has a yield of 90% and a purity of 96%.

<Application Example 1>

Polymer, Resin Composition, and Product:

1 mol of BPADA, 0.93 mol of APBP, and 0.05 mol of the diamine compound represented by Formula (1-1) were mixed to form a mixture. Then, NMP was added into the mixture to form a composition, in which the mixture was present in an amount of 15 wt % based on a total weight of the composition. Next, the composition was stirred under room temperature to permit a reaction for 12 hours so as to obtain a resin composition including a polyamic acid. Thereafter, the resin composition was spin-coated on a glass plate and heated to a temperature of 230° C. to permit a cyclization reaction for 2.5 hours, followed by drying so as to obtain a polyimide film having a thickness of 10 μm.

<Application Examples 2 to 7>

The procedures for manufacturing the polymers, the resin compositions, and the polyamic acid films of Application Examples 2 to 7 were similar to those of Application Example 1, except that the types and amounts of chemicals used were varied as listed in Tables 1 and 2.

<Application Example 8>

267.7 g of thionyl chloride ($SOCl_2$) was gradually added into 1901.6 g of a dicarboxylic acid compound solution (which includes 570.5 g of a dicarboxylic acid compound represented by a formula of 332.2 g of pyridine, and 998.9 g of NMP) using a dropper, followed by a reaction under stirring at a temperature of 0° C. for 2 hours to form a first solution. Then, a second solution, which includes 325.3 g of APBP, 20.4 g of the diamine compound represented by Formula (1-1), and 2903.5 g of NMP, was gradually added into the first solution to form a composition. Next, the composition was subjected to a polymerization reaction for 6 hours so as to obtain a polyamic ester.

Subsequently, 1 part by weight of the polyamic ester, 0.15 part by weight of triethylene glycol dimethacrylate, and 0.03 part by weight of Irgacure® OXE-01 (Manufacturer: BASF Corporation) were mixed to form a mixture, followed by adding NMP into the mixture to form a resin composition, in which the mixture was present in an amount of 25 wt % based on a total weight of the resin composition. Thereafter, the resin composition was spin-coated on a glass plate and heated to a temperature of 230° C. to permit a cyclization reaction for 2.5 hours, followed by drying so as to obtain a polyimide film having a thickness of 10 μm.

<Comparative Application Example 1>

1 mol of BPADA and 0.98 mol of APBP were mixed to form a mixture. Then, NMP was added into the mixture to form a first solution, in which the mixture was present in an amount of 15 wt % based on a total weight of the first solution. Next, the first solution was subjected to a reaction under stirring at room temperature for 12 hours so as to form a second solution including a polyamic acid. Thereafter, 10 g of the second solution and 0.3 g of 3,3',5,5'-tetrakis (methoxymethyl)-(1,1'-biphenyl)-4,4'-diol were mixed to form a mixed liquid. Subsequently, the mixed liquid was spin-coated on a glass substrate and heated to 230° C. to permit a cyclization reaction for 2.5 hours, followed by drying so as to obtain a polyimide film having a thickness of 10 μm.

a second solution including a polyamic acid. Thereafter, the second solution was spin-coated on a glass substrate and heated to 230° C. to permit a cyclization reaction for 2.5 hours, followed by drying so as to obtain a polyimide film having a thickness of 10 μm.

<Evaluations>

Figure 1:
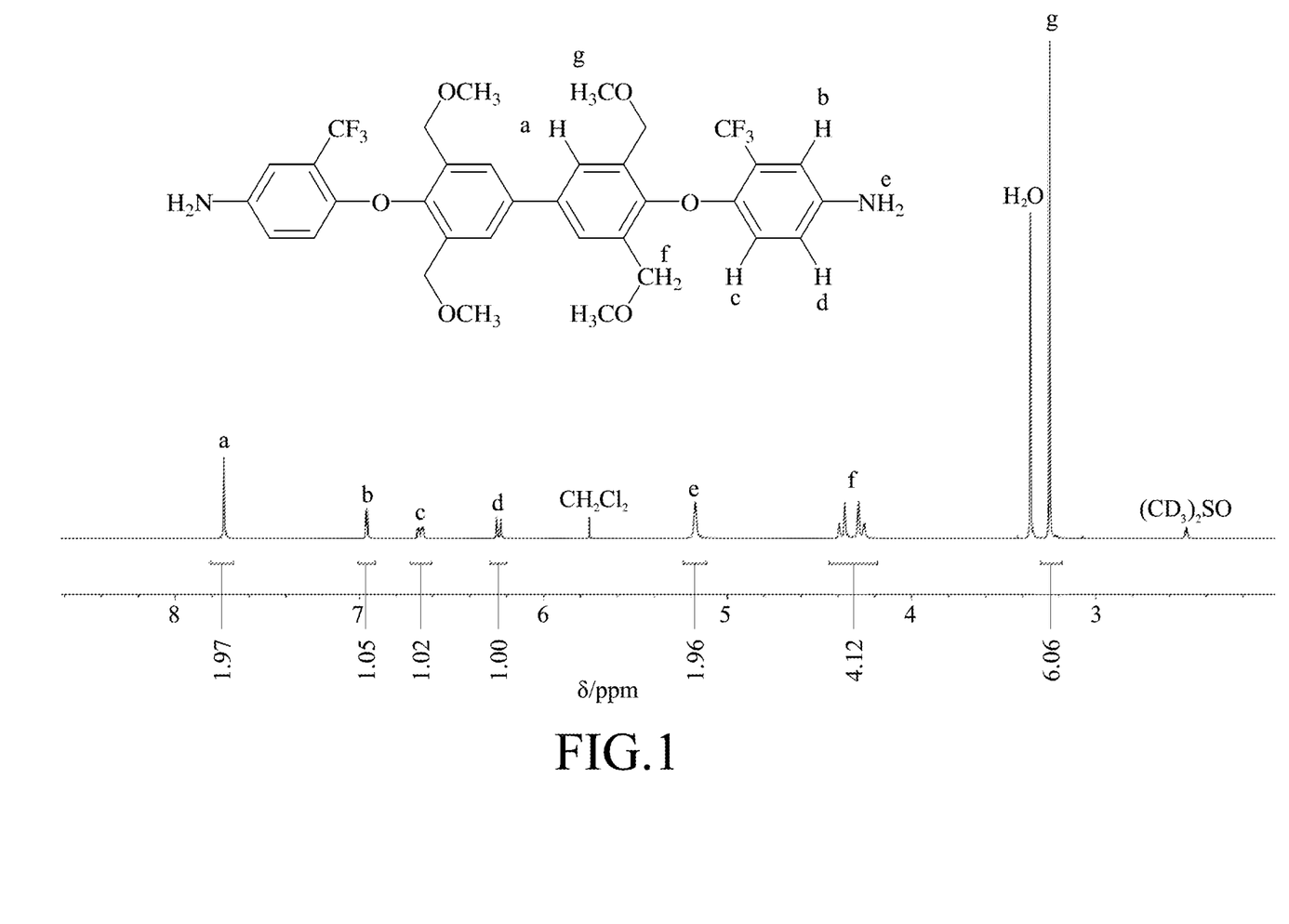
FIG. 1 is a nuclear magnetic resonance (NMR) spectrum of Example 1 of a diamine compound according to the disclosure.
Figure 2:
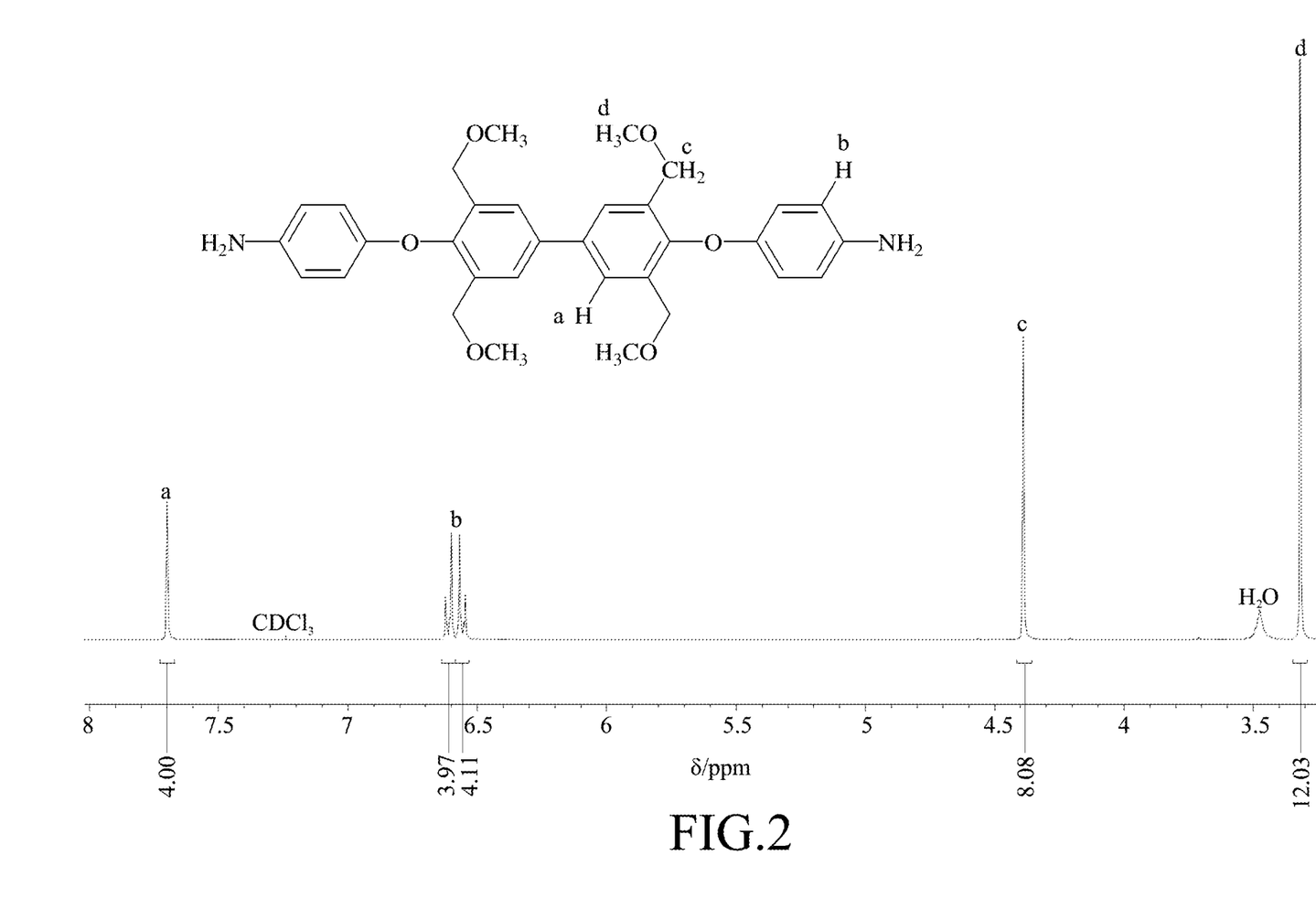
FIG. 2 is an NMR spectrum of Example 2 of the diamine compound according to the disclosure.
Figure 3:
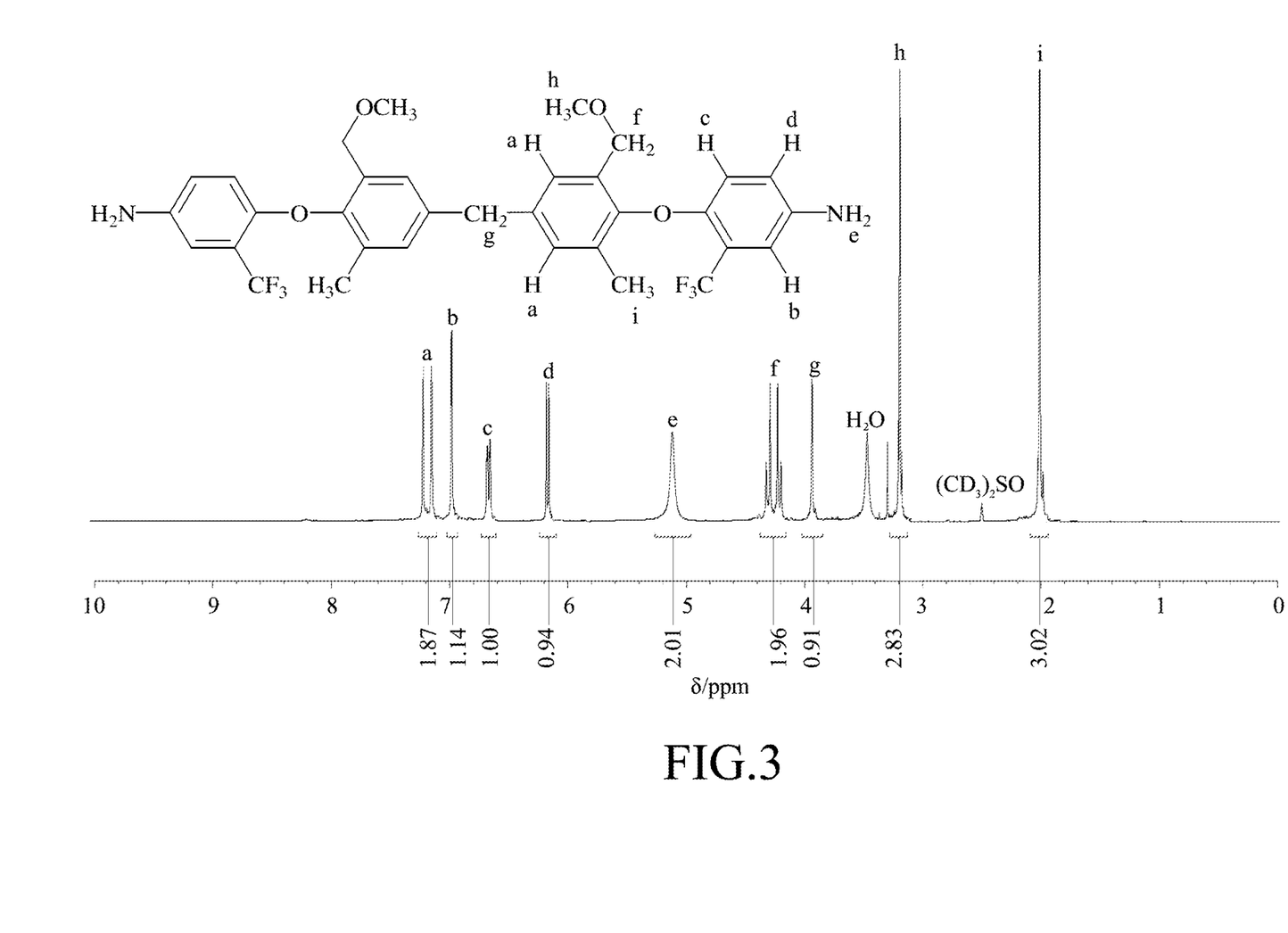
FIG. 3 is an NMR spectrum of Example 3 of the diamine compound according to the disclosure.

1. Structural Analysis:

Each of the diamine compounds of Examples 1 to 3 was analyzed with a nuclear magnetic resonance (NMR) spectrometer to obtain an NMR spectrum as shown in FIGS. 1 to 3. A deuterated NMR solvent used for Examples 1 and 3 was $(CD_3)_2SO$, and a deuterated NMR solvent used for Example 2 was $CDCl_3$. It should be noted that, the characteristic peak of $NH_2$ of Example 2 is not observable in the corresponding NMR spectrum (i.e., FIG. 2) due to a solvent effect caused by $CDCl_3$.

2. Young's Module (GPa), Tensile Strength (MPa), and Elongation at Break (I):

The polyimide films of Application Examples 1 to 8 and Comparative Application Examples 1 to 5 were cut to obtain test samples each having a size of 7 cm (length)×1 cm (width). Then, each of the test samples was measured with an universal testing machine (Manufacturer: Shimadzu Corp.; Model: EZ TESTER-L) under a stretching rate of 1 cm.

|  |  | Application Examples | | | | | | | |
|---|---|---|---|---|---|---|---|---|---|
|  |  | 1 | 2 | 3 | 4 | 5 | 6 | 7 | 8 |
| Diamine component | Diamine compound of Example 1 (mol) | 0.05 | 0.01 | 0.03 | 0.05 | 0 | 0 | 0 | 0.03 |
|  | Diamine compound of Example 2 (mol) | 0 | 0 | 0 | 0 | 0.02 | 0 | 0 | 0 |
|  | Diamine compound of Example 3 (mol) | 0 | 0 | 0 | 0 | 0 | 0.03 | 0.03 | 0 |
|  | APBP (mol) | 0.93 | 0 | 0 | 0 | 0 | 0 | 0 | 0.88 |
|  | DABP (mol) | 0 | 0.97 | 0.95 | 0.93 | 0.96 | 0.95 | 0 | 0 |
|  | BAPP (mol) | 0 | 0 | 0 | 0 | 0 | 0 | 0.95 | 0 |
| Dianhydride compound | BPADA (mol) | 1 | 1 | 1 | 1 | 1 | 1 | 0 | 0 |
|  | ODPA (mol) | 0 | 0 | 0 | 0 | 0 | 0 | 1 | 0 |
| Crosslinking agent | 3,3',5,5'-tetrakis (methoxymethyl)-(1,1'-biphenyl)-4,4'-diol (g) | 0 | 0 | 0 | 0 | 0 | 0 | 0 | 0 |
| Dicarboxylic acid compound (mol) |  | 0 | 0 | 0 | 0 | 0 | 0 | 0 | 1 |
| Evaluations | Young's module (GPa) | 1.56 | 1.56 | 1.53 | 1.45 | 1.52 | 1.6 | 2.15 | 1.50 |
|  | Tensile strength (MPa) | 86.3 | 96.8 | 93 | 84.7 | 95.1 | 99 | 130 | 87.5 |
|  | Elongation at break (%) | 140.1 | 132.4 | 165.8 | 104.5 | 118.7 | 163.9 | 138.2 | 85.1 |

<Comparative Application Examples 2 and 3>

The procedures for manufacturing the polymers, the resin compositions, and the polyimide films of Comparative Application Examples 2 and 3 were similar to those of Comparative Application Example 1, except that the types and amounts of chemicals used were varied as listed in Table 2.

<Comparative Application Example 4>

1 mol of BPADA, 0.95 mol of APBP, and 0.03 mol of 3,5-diaminobenzoic acid 2-(methacryloyloxy)ethyl ester (hereinafter abbreviated as HEMA-DA) were mixed to form a mixture. Then, NMP was added into the mixture to form a first solution, in which the mixture was present in an amount of 15 wt % based on a total weight of the first solution. Next, the first solution was subjected to a reaction under stirring at room temperature for 12 hours so as to form

TABLE 2

|  |  | Comparative Application Examples | | | |
|---|---|---|---|---|---|
|  |  | 1 | 2 | 3 | 4 |
| Diamine component | Diamine compound of Example 1 (mol) | 0 | 0 | 0 | 0 |
|  | Diamine compound of Example 2 (mol) | 0 | 0 | 0 | 0 |
|  | Diamine compound of Example 3 (mol) | 0 | 0 | 0 | 0 |
|  | APBP (mol) | 0.98 | 0 | 0 | 0.95 |
|  | DABP (mol) | 0 | 0.98 | 0 | 0 |
|  | BAPP (mol) | 0 | 0 | 0.98 | 0 |
|  | HEMA-DA (mol) | 0 | 0 | 0 | 0.03 |

TABLE 2-continued

|  |  | Comparative Application Examples | | | |
|---|---|---|---|---|---|
|  |  | 1 | 2 | 3 | 4 |
| Dianhydride compound | BPADA (mol) | 1 | 1 | 0 | 1 |
|  | ODPA (mol) | 0 | 0 | 0 | 0 |
| Crosslinking agent | 3,3',5,5'-tetrakis(methoxymethyl)-(1,1'-biphenyl)-4,4'-diol (g) | 0.3 | 0.3 | 0.3 | 0 |
| Evaluations | Young's module (GPa) | 1.59 | 1.51 | 2.1 | 1.5 |
|  | Tensile strength (MPa) | 95.7 | 90.4 | 132.8 | 87.3 |
|  | Elongation at break (%) | 13.1 | 14.7 | 18.5 | 20.6 |

Based on the results shown in Tables 1 and 2, each of the polyimide films of Comparative Application Examples 1 to 4 exhibits a relatively low elongation at break that ranges from 13.1% to 20.6% since each of the diamine components used in Comparative Application Examples 1 to 4 does not include a diamine compound having the (chain alkoxy-methylene) phenyl group. In comparison, each of the polyimide films of Application Examples 1 to 8 exhibits a relatively high elongation at break ranging from 85.1% to 165.8%. In addition, while the elongations at break are improved, mechanical strengths (i.e., young's module and tensile strength) of the polyimide films of Application Examples 1 to 8 are approximately the same as those of the polyimide films of Comparative Application Examples 1 to 4. Therefore, it can be concluded that by formation of the polyimide film with a diamine component which includes a diamine compound having the (chain alkoxy-methylene) phenyl group, the polyimide film may have an improved elongation at break while maintaining the mechanical strengths thereof.

Further, as shown in Table 1, the polyimide film of Application Example 3, which is made from the diamine component including the diamine compound of Example 1 (which has 4 methoxymethylene groups), has an elongation at break of 165.8%. In comparison, the polyimide of Application Example 6, which is made from the diamine component including the diamine compound of Example 3 (which has 2 methoxymethylene groups), has an elongation at break of 163.9%. Therefore, it can be concluded that an increased number of the methoxymethylene group in the diamine compound may also improve the elongation at break of the polyimide films.

In sum, by inclusion of the (chain alkoxy-methylene) phenyl group in the diamine compound of this disclosure, a polymer made from a diamine component including the diamine compound may have a satisfactory elongation at break and mechanical strength.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A diamine compound represented by Formula (1),

Formula (1)

wherein
each of $R^1$ and $R^2$ represents a single bond;
each of $R^3$, $R^4$, and $R^5$ represents independently a single bond, a methylene group, an ethylene group, a propylene group, a butylene group, an isopropylene group, a 1-ethyl-propylene group, a 1,1-dimethyl-propylene group, a 1,2-dimethyl-propylene group, a 2,2-dimethyl-propylene group, a 1-ethyl-1-methyl-propylene group, a 1-ethyl-2-methyl-propylene group, a 1,1,2-trimethyl-propylene group, a 1,2,2-trimethyl-propylene group, a sec-butylene group, an isobutylene group, a —S— group, a —O— group, group, a —C(CF$_3$)$_2$— group, or a —SO$_2$— group;
each of $X^1$, $X^2$, $X^3$, and $X^4$ represents independently hydrogen, a —CH$_2$—O—T$^2$ group, a methyl group, an ethyl group, a propyl group, an isopropyl group, a fluoro group, or a —CF$_3$ group, wherein T$^2$ in the —CH$_2$—O—T$^2$ group represents hydrogen or a chain alkyl group;
each of m and n is independently an integer of from 0 to 6, wherein 1≤m+n≤2; and
each of a, b, c, and d is independently an integer of from 0 to 4,
with the proviso that
when m>1, $R^4$s are the same or different,
when n>1, $R^5$s are the same or different,
when the number of T$^2$ is plural, T$^2$s are the same or different,
when a>1, $X^1$s are the same or different,
when b>1, $X^2$s are the same or different,
when c>1, $X^3$s are the same or different,
when d>1, $X^4$s are the same or different,
at least one of a, b, c, and d is not 0,
at least one of $X^1$, $X^2$, $X^3$, and $X^4$ is a —CH$_2$—O—CH$_3$ the group, and
said diamine compound does not include a compound represented by a structural formula of 2. The diamine compound according to claim 1, which includes a plurality of the —CH$_2$—O-T$^2$ groups.

3. The diamine compound according to claim 2, wherein T$^2$ is a —CH$_3$ group.

4. The diamine compound according to claim 1, wherein each of R$^4$ and R$^5$ is the —O— group.

5. The diamine compound according to claim 1, wherein each of X$^1$ and X$^2$ is not the —CH$_2$—O-T$^2$ group.

6. A method for manufacturing a diamine compound, the method comprising:
 a) subjecting a compound represented by Formula (a) and a compound represented by Formula (b) to a reaction so as to obtain a compound represented by Formula (2); and
 b) subjecting the compound represented by Formula (2) to a reduction reaction so as to obtain a compound presented by Formula (1), group, a —C(CF$_3$)$_2$— group, or a —SO$_2$— group;
 each of m and n is independently an integer of from 0 to 6, wherein 1≤m+n≤2; and
 each of a, b, c, and d is independently an integer of from 0 to 4,
 with the proviso that
  when m>1, R$^4$s are the same or different,
  when n>1, R$^5$s are the same or different,
  when the number of T$^2$ is plural, T$^2$s are the same or different,
  when a>1, X$^1$s are the same or different,
  when b>1, X$^2$s are the same or different,
  when c>1, X$^3$s are the same or different,
  when d>1, X$^4$s are the same or different,
  at least one of a, b, c, and d is not 0, and
  at least one of X$^1$, X$^2$, X$^3$, and X$^4$ is a —CH$_2$—O—CH$_3$ group.

7. A composition for forming a polymer, comprising a diamine component which includes the diamine compound according to claim 1.

wherein
R represents R$^1$ or R$^2$, and each of R$^1$ and R$^2$ represents a single bond;
each of Y, Y$^1$, and Y$^2$ represents a leaving group;
X represents (X$^1$)$_a$ or (X$^1$)$_b$;
each of X$^1$, X$^2$, X$^3$, and X$^4$ represents independently a hydrogen, a —CH$_2$—O-T$^2$ group, a methyl group, an ethyl group, a propyl group, an isopropyl group, a fluoro group, or a —CF$_3$ group, wherein T$^2$ in the —CH$_2$—O-T$^2$ group represents hydrogen or a chain alkyl group;
each of R$^3$, R$^4$, and R$^5$ represents independently a single bond, a methylene group, an ethylene group, a propylene group, a butylene group, an isopropylene group, a 1-ethyl-propylene group, a 1,1-dimethyl-propylene group, a 1,2-dimethyl-propylene group, a 2,2-dimethyl-propylene group, a 1-ethyl-1-methyl-propylene group, a 1-ethyl-2-methyl-propylene group, a 1,1,2-trimethyl-propylene group, a 1,2,2-trimethyl-propylene group, a sec-butylene group, an isobutylene group, a —S— group, a —O— group, a 8. A polymer comprising a diamine structural unit formed from the diamine compound according to claim 1.

9. The polymer according to claim 8, which is selected from the group consisting of polyamide, polyamic acid, polyimide, polyamic ester, polyamide-imide, a polybenzoxazole precursor, polybenzimidazole, polybenzoxazole, and copolymers thereof.

10. A resin composition comprising the polymer of claim 8.

11. A resin composition comprising the polymer of claim 9.

12. A product made from the resin composition of claim 10.

13. A product made from the resin composition of claim 11.

14. An electronic device comprising the product of claim 12.

15. The electronic device according to claim 14, which is a semiconductor device or a display device.

16. An electronic device comprising the product of claim 13.

17. The electronic device according to claim 16, which is a semiconductor device or a display device.

\* \* \* \* \*